(12) United States Patent
Yoder

(10) Patent No.: US 7,811,019 B2
(45) Date of Patent: Oct. 12, 2010

(54) SANITARY DISPOSABLE WRITING INSTRUMENT, METHOD OF MAKING, AND DISPENSER THEREFORE

(76) Inventor: Timothy Howard Yoder, 700 H Springfield Rd., Columbiana, OH (US) 44408

( * ) Notice: Subject to any disclaimer, the term of this patent is extended or adjusted under 35 U.S.C. 154(b) by 1190 days.

(21) Appl. No.: 11/412,027

(22) Filed: Apr. 26, 2006

(65) Prior Publication Data
US 2008/0043048 A1 Feb. 21, 2008

Related U.S. Application Data

(60) Provisional application No. 60/675,200, filed on Apr. 27, 2005.

(51) Int. Cl.
*A46B 5/02* (2006.01)
*B43K 25/00* (2006.01)
*B43K 29/00* (2006.01)
(52) U.S. Cl. .............................. 401/6; 401/52; 401/195
(58) Field of Classification Search ...................... 401/6, 401/28, 52, 144, 195
See application file for complete search history.

(56) References Cited

U.S. PATENT DOCUMENTS

| | | | | |
|---|---|---|---|---|
| 1,208,701 A | * | 12/1916 | Trenner | 206/440 |
| 2,465,876 A | * | 3/1949 | Hornung | 221/72 |
| 3,168,072 A | * | 2/1965 | Nitta | 401/97 |
| 4,243,338 A | * | 1/1981 | Williams | 101/195 |
| 4,738,556 A | * | 4/1988 | Brown | 401/7 |
| 5,399,041 A | * | 3/1995 | Chiswell | 401/209 |
| 5,683,655 A | | 11/1997 | Carter | 422/28 |
| 5,722,575 A | * | 3/1998 | Smith | 224/217 |
| 5,755,355 A | * | 5/1998 | Timmerman et al. | 221/33 |
| 2003/0185615 A1 | * | 10/2003 | Smith | 401/6 |
| 2004/0003521 A1 | * | 1/2004 | Penn et al. | 40/299.01 |

OTHER PUBLICATIONS

Rover, Elena, "The Cold Wars", Real Simple Magazine, Dec. 2005-Jan. 2006 Issue, pp. 203-204.
Papermate® Advertisement "Guard Against Gross", Flexgrip Elite® anti-bacterial pen protection.

* cited by examiner

*Primary Examiner*—Gregory L Huson
*Assistant Examiner*—Ryan A Varnum
(74) *Attorney, Agent, or Firm*—The Webb Law Firm

(57) ABSTRACT

A sanitary disposable writing instrument for minimizing the transfer of bacteria, viruses and/or chemicals from one person to another is provided. The sanitary disposable writing instrument comprises a strip of flexible holding material having a writing implement with a writing tip attached to the flexible material. A grasping means is formed from a portion of the holding material. This grasping means allows the user to grasp the writing implement to write with the writing tip. The disposable writing instruments are provided in a series of instruments that may be removed, used, and disposed of leaving a subsequent, untouched sanitary writing instrument in place for the next user. A dispenser for dispensing these writing instruments and a method of making such instruments is also provided in this invention.

9 Claims, 7 Drawing Sheets

US 7,811,019 B2

SANITARY DISPOSABLE WRITING INSTRUMENT, METHOD OF MAKING, AND DISPENSER THEREFORE

CROSS-REFERENCES TO RELATED APPLICATIONS

This application is related to Provisional Application Ser. No. 60/675,200, filed Apr. 7, 2005.

FIELD OF THE INVENTION

This invention is related to the field of sanitary disposable articles and, more particularly, to a sanitary disposable writing instrument, a method of making such writing instrument, and a dispenser therefore, to prevent cross-contamination of bacteria, viruses and/or chemicals from one person to another in public locations.

BACKGROUND OF THE INVENTION

Numerous studies have been performed to determine the levels of bacteria or microbes found on commonly used products. It has been found that one of the highest levels of bacteria can be found on writing instruments used by the public in medical environments such as doctor offices, medical clinics, or hospitals, or other high traffic areas such as hotels, cruise ships, banks, restaurants, stores and the like. In medical environments, when a patient is signing the register or writing down his/her medical history, patients who are usually ill, commonly use the same writing instrument. Transference of bacteria, viruses and/or chemicals can occur between medical personnel amongst themselves, as well as, with other patients. In other public environments, such as hotels, restaurants, or banks, people, who may have a cold or the flu, commonly use the same writing instrument. Thus, cross-contamination of germs from one person to another is very common.

In an article entitled "The Cold Wars" in the December 2005-January 2006 edition of *Real Simple* magazine, the author states that as a means of preventing colds and the flu, one should "keep hands clean by avoiding well-handled objects like the pens at banks and restaurants (bring your own)". Papermate® has also recently developed a product called the FlexGrip® Elite which is a pen having anti-bacterial protection. This product is being marketed as a device to "Guard Against Gross" which is supposed to keep the pen's surface bacteria free.

U.S. Pat. No. 5,683,655 is directed to an apparatus and method for disinfecting writing instruments for health care professionals which includes a holding means containing disinfecting fluid, an absorbent material pad which is moistened with the disinfecting fluid and a series of slits through the disinfecting pad which enable the writing instrument to be passed there through for disinfecting. While this type of device can eliminate the problem of cross-contamination of germs through use of the writing instrument, such device is costly and bulky to move about the office. Also, this device would require routine maintenance thereof and the purchase and replacement of additional disinfecting fluid.

There is a need in the art for an economically feasible single-use writing instrument, which can reduce and/or eliminate the cross-contamination of germs from one person to another when using these "well-handled" objects such as in banks, restaurants, cruise ships, hotels and the like. There is an even greater need in the art for an economically feasible single-use writing instrument in the medical field that can eliminate cross-contamination of bacteria, viruses and chemicals from one patient to another, from healthcare professionals to patients, and from patients back to healthcare professionals. There is also a need in the art for an economically feasible single-use writing instrument the can be used in a "clean" manufacturing environment such as in pharmaceutical manufacturing plants or chemical laboratories. There is also a need in the art for a dispenser for dispensing these writing instruments, which will minimize the transfer of bacteria, viruses and/or chemicals from person to person.

OBJECTS OF THE INVENTION

It is therefore a primary object of the invention to provide a sanitary disposable writing instrument that will minimize the cross-contamination of bacteria, viruses, chemicals and the like from one person to another.

It is a further object of the invention to provide a sanitary disposable writing instrument that is useful in the medical field to minimize the transference of germs, viruses, chemicals and diseases from patient to patient, patient to medical personnel and vice versa, and medical personnel to other medical personnel.

It is another object of the invention to provide a sanitary disposable writing instrument that prevents the transference of germs and bacteria between people at public locations such as banks, restaurants, hotels, cruise ships, stores and the like.

It is another object of the invention to provide a sanitary disposable writing instrument that may be used in "clean" manufacturing plants such as pharmaceutical plants and chemical laboratories.

It is yet another object of the invention to provide a sanitary disposable writing instrument that is functional and economically feasible to produce and dispose of after a single use.

It is another object of the invention to provide a sanitary disposable writing instrument that can be conveniently sized so that it may be placed in a variety of locations.

It is an even further object of the invention to provide a sanitary disposable writing instrument that may have an advertisement or coupon removably attached thereto which would supplement the cost of the writing instrument.

It is another object of the invention to provide a dispenser for dispensing a series of sanitary disposable writing instruments that prevents contamination of the writing instruments prior to their individual use.

It is a further object of the invention to provide a mechanically simple, low cost dispenser that allows for easy loading of the series of writing instruments and ready removal therefrom of individual writing instruments.

It is yet another object of the invention to provide a method for forming a series of sanitary disposable writing instruments.

In addition to the various objects and advantages of the invention which have been described in some specific detail above, it should be noted that various other objects and advantages of the present invention will become more readily apparent to those persons who are skilled in the relevant art from the following more detailed description, particularly, when such description is taken in conjunction with the attached drawing Figures and with the appended claims.

SUMMARY OF THE INVENTION

Briefly, and in accordance with the forgoing objects, the invention comprises a sanitary disposable writing instrument for minimizing the transfer of bacteria, viruses and/or chemicals from one person to another. The sanitary disposable writing instrument comprises a strip of flexible holding material having a predetermined size and shape and a first and second portion. A writing implement is provided which has a first end and a second end. The first end of the writing implement extends along and is secured to the first portion of the holding material. The second end of the writing implement extends beyond and in a perpendicular direction with respect to an edge of the holding material to form a writing tip. A grasping means is formed from one of the second portion and the first portion of the holding material. This grasping means allows the user to grasp the writing implement to write with the writing tip. The disposable writing instruments are provided in a series of instruments in the form of either a continuous strip of material having frangible portions between each instrument for easy separation therefrom or in a stack wherein alternating opposing ends of the instruments are attached to one another by means of a pressure sensitive adhesive.

DETAILED DESCRIPTION OF THE INVENTION

Figure 1:
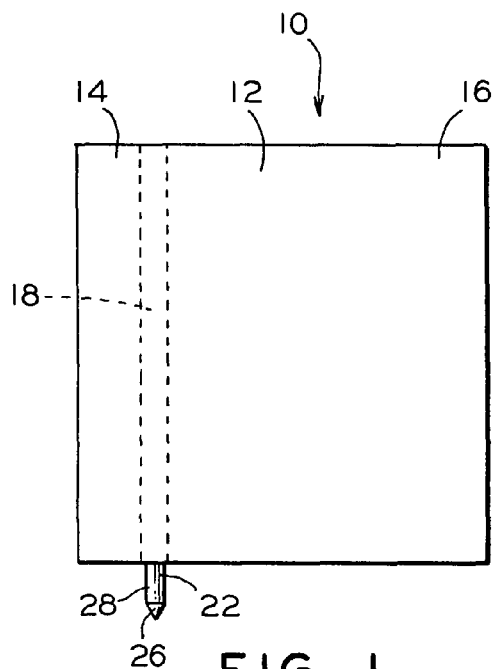
FIG. 1 shows a top view of the sanitary disposable writing instrument according to a first embodiment of the invention.

Before describing the invention in detail, the reader is advised that, for the sake of clarity and understanding, identical components having identical functions have been marked where possible with the same reference numerals in each of the Figures provided in this document.

Referring now to FIGS. 1-2 and 5-6, there is shown the sanitary disposable writing instrument, generally indicated as 10, for reducing the transfer of bacteria, viruses and/or chemicals from one person to another. The sanitary disposable writing instrument 10 comprises a strip of flexible holding material 12 having a predetermined size and shape. The strip of holding material 12 may be formed from any well known material such as paper, plastic, neoprene, and the like. The strip of holding material 12 has a first portion 14 and a second portion 16. A writing implement 18 having a first end 20 and a second end 22 is provided. The first end 20 of the writing implement 18 extends along and is secured to the first portion 14 of the holding material 12. This writing implement 18 is secured to the holding material 12 by any well known means such as adhesive, fusion, and the like. The second end 22 of the writing implement 18 extends beyond and in a perpendicular direction with respect to an edge 24 of the holding material 12 to form a writing tip 26. A writing means 28 is associated with the writing tip. Any well-known writing means may be employed as the writing implement 18 such as a pen, pencil, a marker, and the like. Preferably the writing implement 18 comprises a hollow tube and the writing means comprises either an ink source or graphite filled member, which is capable of being inserted within the hollow tube. A grasping means 30 is formed from one of the second portion 16 and the first portion 14 of the holding material 12. This grasping means 30 acts as an anchor and enables a user to grasp one of the first portion 14 and the second portion 16 of the holding material 12 within his/her hand and write with the writing tip 26.

Figure 2:
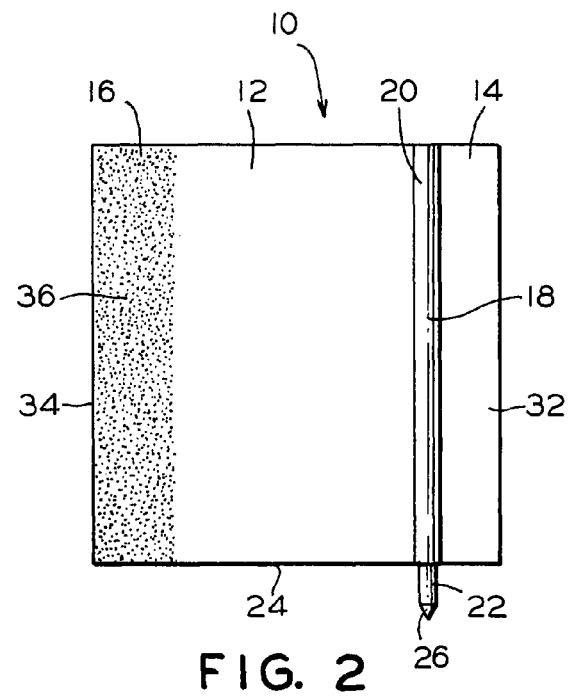
FIG. 2 shows a bottom view of the sanitary disposable writing instrument of FIG. 1.

According to a first embodiment, as illustrated in FIGS. 1-2, the first portion 14 of the holding material 12 can comprise a first edge area 32 of the strip and the second portion 16 of the holding material 12 can comprise a second edge area 34 of the strip 12. A securing means 36, such as a pressure sensitive adhesive, can be provided along the second edge 34 of the holding material.

Figure 4A:
FIG. 4A shows the sanitary disposable writing instrument of FIG. 1 rolled into a final form to produce a grasping portion for a user to grasp and write with the writing instrument.
Figure 4B:
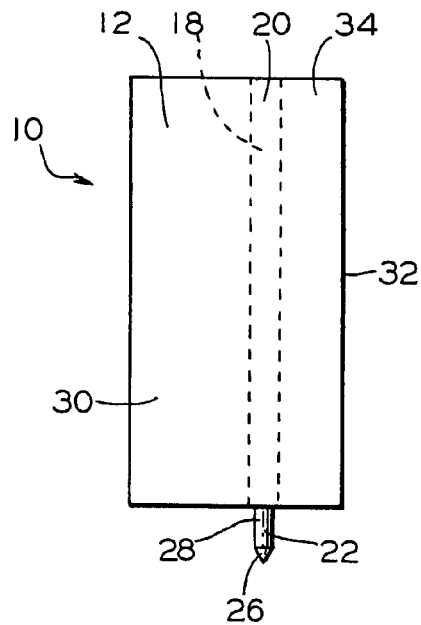
FIG. 4B shows the sanitary disposable writing instrument of FIG. 1 folded into a final form to produce a grasping portion for a user to grasp and write with the writing instrument.

The sanitary disposable writing instrument may be prepared for use by two methods. The first of these methods are shown in FIG. 4A wherein the second edge area 34 is rolled up into a cylinder 38 to enclose the writing implement 10 therein and to form an area for the user to grasp the instrument. The second edge area 34 is secured by means of the pressure sensitive adhesive 36. The second method of preparation is shown in FIG. 4B. This method can be employed for users who are in a hurry and may only need to use the implement to write something quick, such as signing their name. In this method, the user simply folds the second edge area 34 onto the first edge area 32 to enclose the writing implement and form the grasping means 30. Again, the pressure sensitive adhesive 36 provided on the second edge area 34 secures the second portion 16 of the strip 12 to the first portion 14.

Figure 4C:
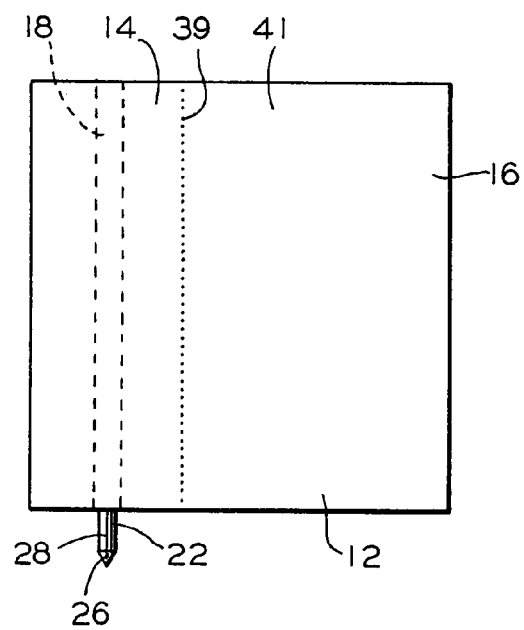
FIG. 4C shows the sanitary disposable writing instrument of FIG. 1 wherein a portion of the writing instrument is removable to form a coupon or advertisement.

As shown in FIG. 4C, a modification may be made to the sanitary disposable writing instrument wherein the first portion 14 of the holding material 12 comprises a first edge area 32 of the strip 12. This first edge area 32 of the strip is capable of being one of folded and rolled to enclose the writing implement 18 and to form the grasping means 30. The second portion 16 of the holding material 12 is removable from the first portion by means of a frangible and/or perforated area 39 extending between the first 14 and second 16 portion. This second portion 16 which can be removed from the first portion 14 can be in the form of a coupon or advertisement 41 that the pen user may remove from the sanitary disposable writing instrument. Note that although the pressure sensitive adhesive would not be available for securing this first portion 14 in place, this first portion 14 of the material 12 can be held by the user simply by the action of writing with the instrument 10. This advertising product could supplement the cost of the disposable writing instruments and provide a novel technique for store, restaurant, and hotel owners to advertise their product as well as reduce their cost of purchasing the disposable writing instruments.

Figure 3:
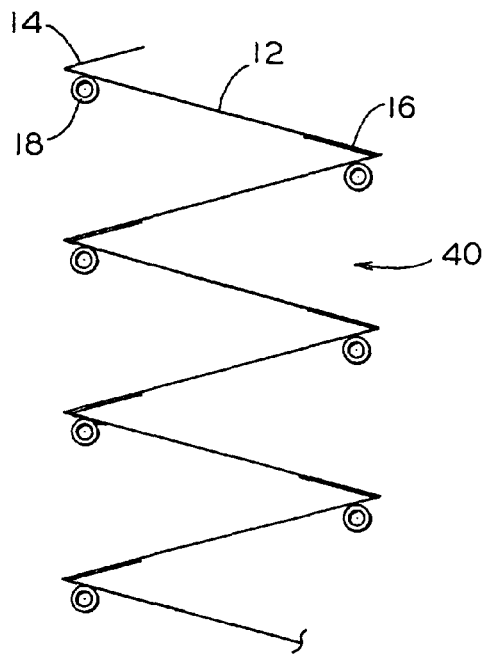
FIG. 3 shows a series of the sanitary disposable writing instrument of FIG. 1.

As shown in FIG. 3, at least a second writing instrument 10 may be secured thereto to form a series, generally indicated as 40, of sanitary disposable writing instruments 10. This series 40 of sanitary disposable writing instruments 10 are preferably secured to one another by means of the pressure sensitive adhesive strip 36 which runs along the second edge area 34 of the holding material 12.

Figure 6:
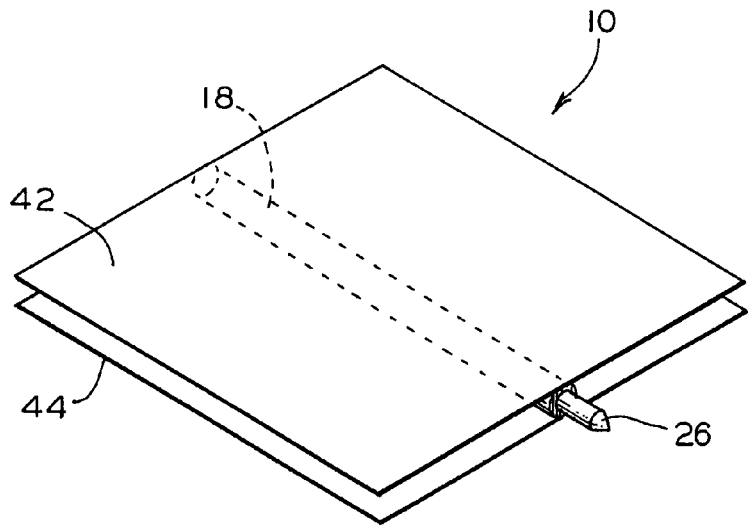
FIG. 6 shows a side view of the sanitary disposable writing instrument of FIG. 5.
Figure 5:
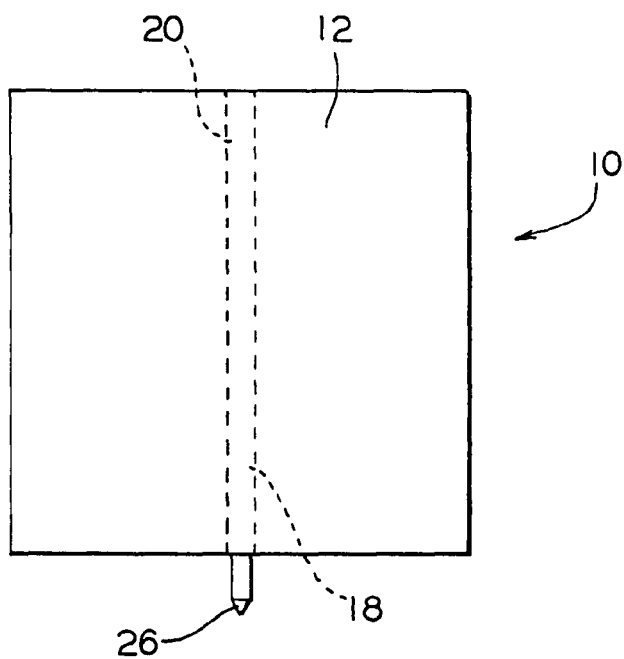
FIG. 5 shows a top view of the sanitary disposable writing instrument according to a second embodiment of the invention.
Figure 7A:
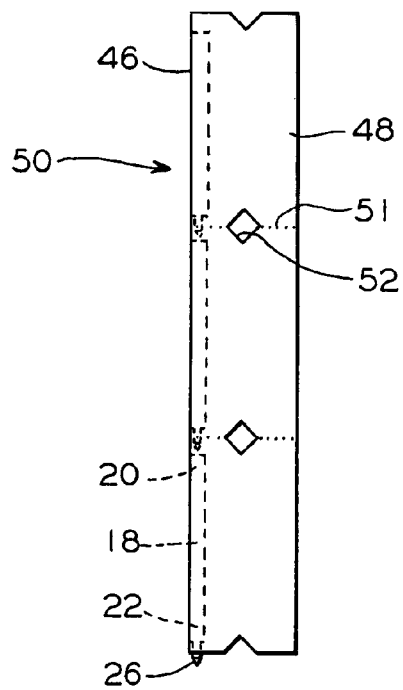
FIG. 7A shows a series of the sanitary disposable writing instruments of FIGS. 5 and 6 wherein the writing implement is positioned along a side portion of the holding material.
Figure 7B:
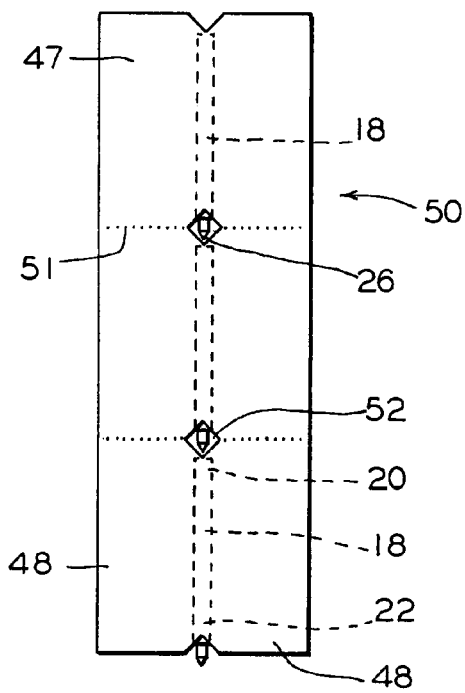
FIG. 7B shows a series of the sanitary disposable writing instruments of FIGS. 5 and 6 wherein the writing implement is positioned along a center portion of the holding material.

According to an alternative embodiment as illustrated in FIGS. 5-6, the strip of holding material 12 can comprise a pair of layers 42, 44 and the writing implement 18 is enclosed and sealed between these layers 42, 44. These layers may be sealed by any well-known means, such as adhesive, plastic fusion, and the like. As shown in FIGS. 7A and 7B, the first portion 14 of the strip 12, which holds the writing implement 18, can either be an edge portion 46 or a center portion 47. The second portion 16 can be the surrounding portion 48 of the holding material 12 that assists the user in grasping the writing instrument.

According to this embodiment, multiple writing instruments 10 may be secured to one another to form a series, generally indicated as 50. The instruments 10 are secured to one another by means of frangible and/or perforated areas 51 between the strip of flexible material 12. A slit 52 in the frangible area 51 is provided to assist in the separation of the individual writing instruments 10. In the design wherein the writing implement 18 extends along a center portion 47 of the layers 42, 44 this slit is provided in the area of the writing tip 26. In the design of the writing instrument wherein the writing implement 18 extends along an edge portion 46 of the layers 42, 44 this slit should still be provided in the center of the frangible area 51 to allow for easy and even separation of the writing instrument 10 from the subsequent instrument 10 in the series 50.

A dispenser, as illustrated in FIGS. 8-14 is provided for dispensing the series of sanitary writing instruments 10. The dispenser comprises a container 53 having a size and shape capable of holding a series of writing instruments 40, 50 and preventing contamination of the writing instruments. An open portion 54 is provided in the container 53. This open portion 54 has a size and shape capable of feeding the series of writing instruments there through and allowing a user to remove a single writing instrument from the container and to leave a subsequent writing instrument in a position for removal from the open portion 54.

Figure 10:
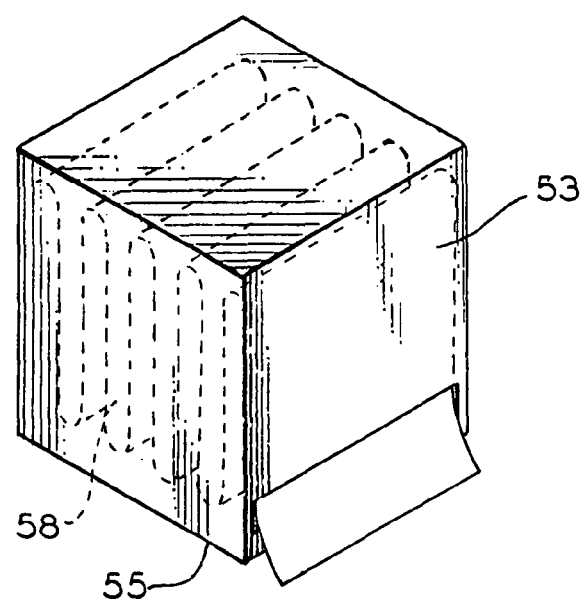
FIG. 10 shows the dispenser of FIG. 8 including a series of the sanitary disposable writing instruments accordion folded within the dispenser.
Figures 8, 9:
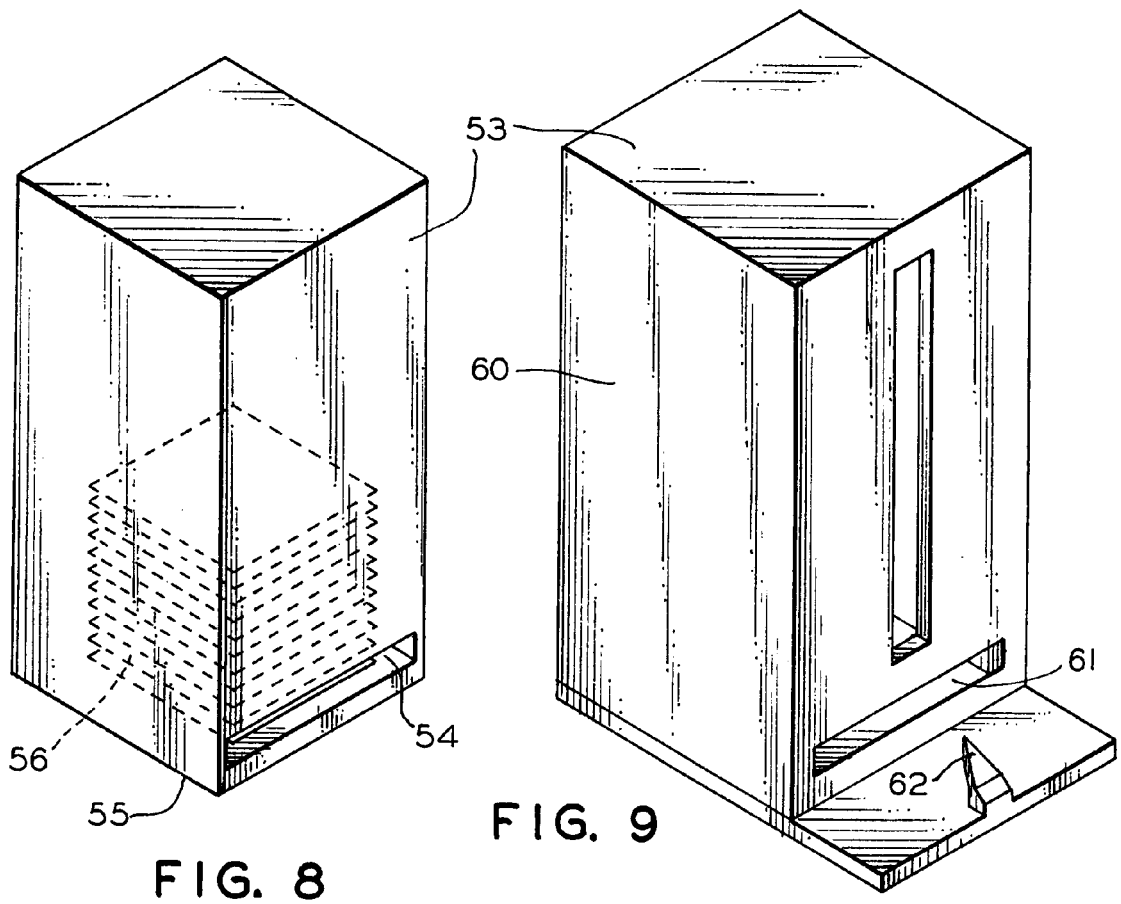
FIG. 8 shows a side perspective view of a dispenser for dispensing a series of the sanitary disposable writing instruments according to a first embodiment.
FIG. 9 shows a holding means for the dispenser of FIG. 8.

According to a first embodiment as illustrated in FIGS. 8 and 10, the size and shape of said container 53 is a box. This box is capable of holding a series of writing instruments in two forms. The open portion 54 is provided on a bottom portion 55 of the box 53. The first form is a stack 56 of separated double layer writing instruments, as illustrated in FIGS. 5-6, which are positioned in the box and fed from the bottom open portion 54. Another form is shown in FIG. 10 wherein a series of the double layer writing instruments are provided in attached form, such as those in FIGS. 7A and 7B. A group of approximately ten to twelve individual instruments are accordion folded onto one another 58 and fed through the bottom open portion 54 of the container 53. In these two methods, subsequent writing instruments are one of fed to the open portion 54 by gravity and/or are fed to the open portion 54 by the application of a pulling force by the user on a previous writing instrument 10 during removal therefrom.

A holder 60, as shown in FIG. 9 may be provided for holding the box shaped container 53. This holder may be mounted to a surface, such as the wall or a counter. The holder 60 can be formed from a stable material such as plastic or metal so as to sufficiently support the box shaped container 53 and allow for replacement boxes 53 of the writing instruments 10 to be placed therein. A bottom opening 61 is provided which corresponds with the opening 54 of the box shaped container 53. A separating tab 62 is provided on the holder 60. This separating tab 62 extends in a perpendicular direction with respect to the feed of the series of writing instruments 50. The separating tab 62 is capable of entering the slit portion 52 of the frangible area 51 between each of the writing instruments 10 to assist the user in separating a single writing instrument from subsequent writing instruments.

Figure 11:
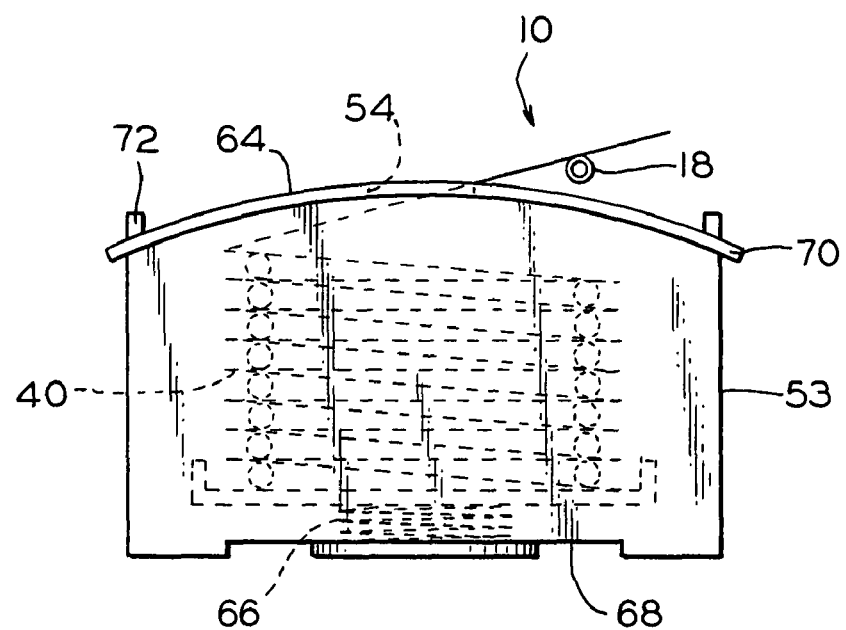
FIG. 11 shows a side view of a dispenser for dispensing a series of the sanitary disposable writing instruments according to a second embodiment.
Figure 12:
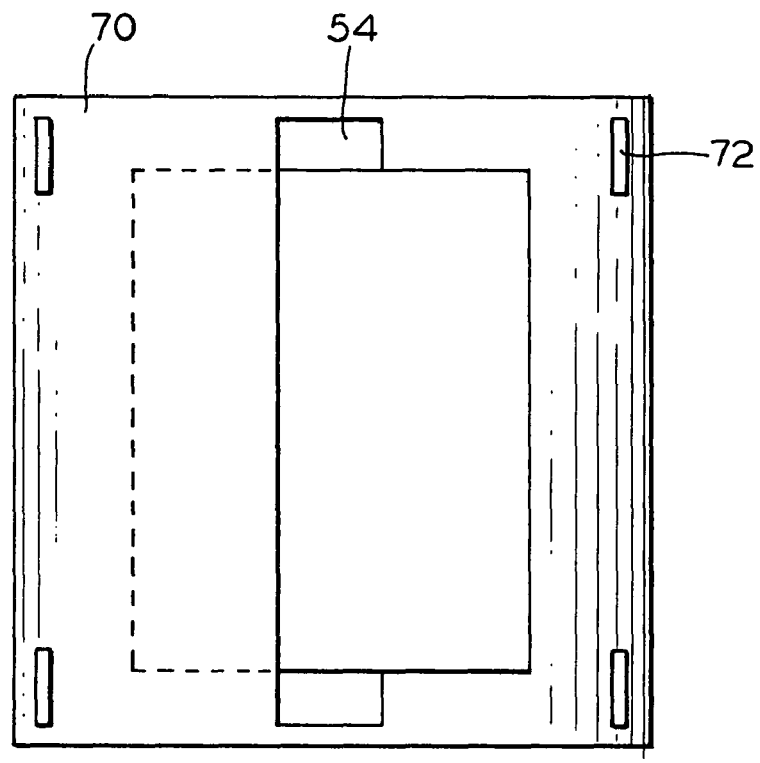
FIG. 12 shows a top view of the dispenser of FIG. 11.

As shown in FIGS. 11-12, according to a second embodiment, the open portion 54 comprises an opening in a top portion 64 of the box shaped container 53. The dispenser further includes a spring 66 in a bottom portion 68 of the box shaped container 53 for applying an upward force to the series 40 of writing instruments in order to feed the instruments 10 through the open portion 54. This dispenser is used primarily for dispensing the series 40 of disposable writing instruments 10 illustrated in FIGS. 1-3 and 4A-4C. This dispenser is designed to have a removable lid 70 secured to the box 53 via locking tabs 72 to enable loading of and/or replacement supplies of the series of writing instruments into the box shaped container 53.

Figure 14:
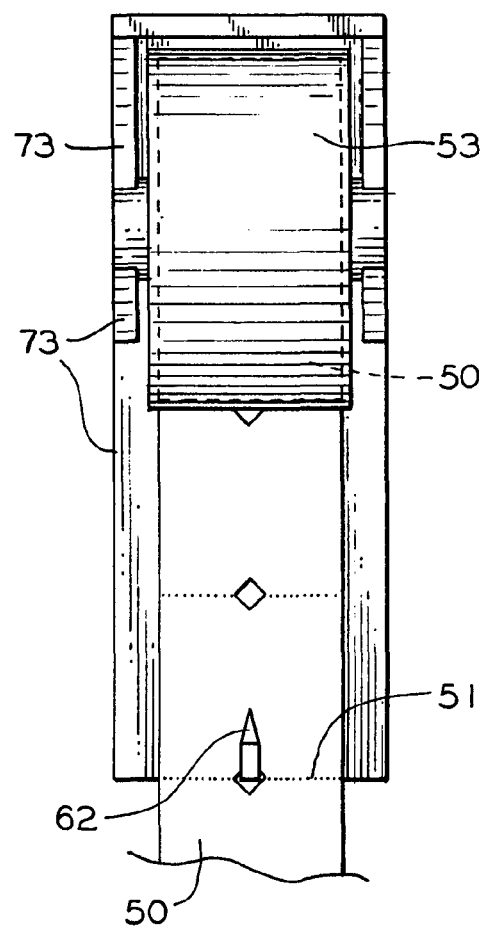
FIG. 14 shows a top view of the dispenser of FIG. 13.
Figure 13:
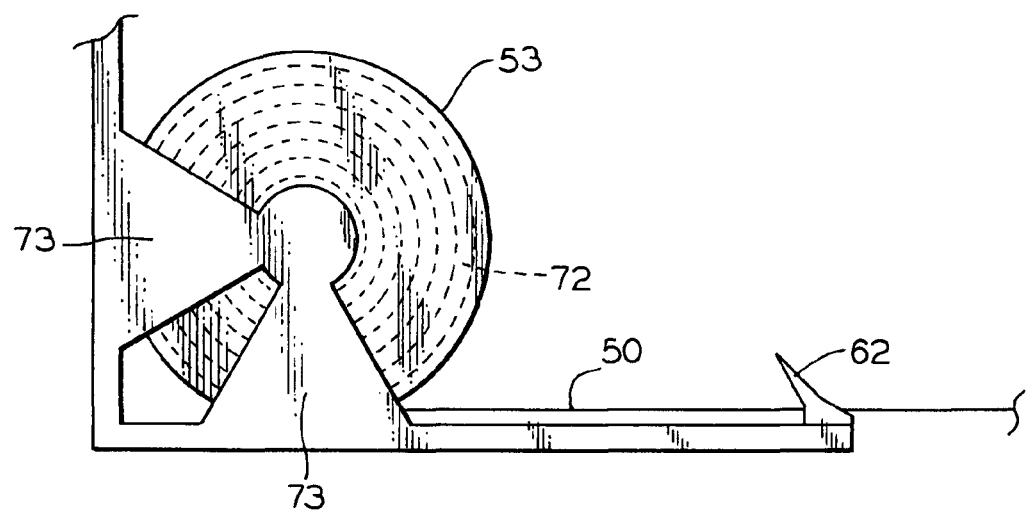
FIG. 13 shows a side view of a dispenser for dispensing a series of the sanitary disposable writing instruments according to a third embodiment.

According to a third embodiment of the dispenser, as shown in FIGS. 13-14, the size and shape of the container 53 is capable of holding a roll 72 of disposable writing instruments 10. Mounting means 73 are provided for holding the roll 72 within the container 53. These mounting means 73 are capable of mounting the roll 72, with or without container 53, onto the wall or on a stand. This embodiment is designed for dispensing the series of writing instruments 50 illustrated in FIGS. 7A and 7B wherein the instruments are supplied as a continuous strip having a frangible area 51 between each of the disposable writing instruments. As stated above, a slit 52 is provided in a portion of the frangible area between the instruments 10, preferably in the center of this area. A separating tab extending in a perpendicular direction with respect to the feed of the series 50 of the writing instruments 10 is capable of entering this slit 52 between each of the writing instruments 10 to assist the user in evenly separating a single writing instrument 10 from subsequent writing instruments in the series.

The present invention also teaches a method of forming a series 40, 50 of disposable writing instruments capable of minimizing the transfer of bacteria, viruses and/or chemicals from one person to another. The method comprises the steps of continuously feeding at least one sheet 74 of holding material 12. Continuously feeding a hollow holding tube 78 in a parallel direction with respect to the at least one sheet 74 of holding material 12. Securing the holding tube 78 to the at least one sheet via the application of adhesive and/or heat via a sealing means 79. Forming frangible areas via a perforating means 80 in the at least one sheet 74 of holding material 12 and the hollow holding tube 78 to form a series of separable writing instruments and inserting a writing source within the hollow holding tube 78. The perforating means 80 or a separate cutting member 81 is provided for cutting the hollow tube into individual writing implements 18.

Figure 15:
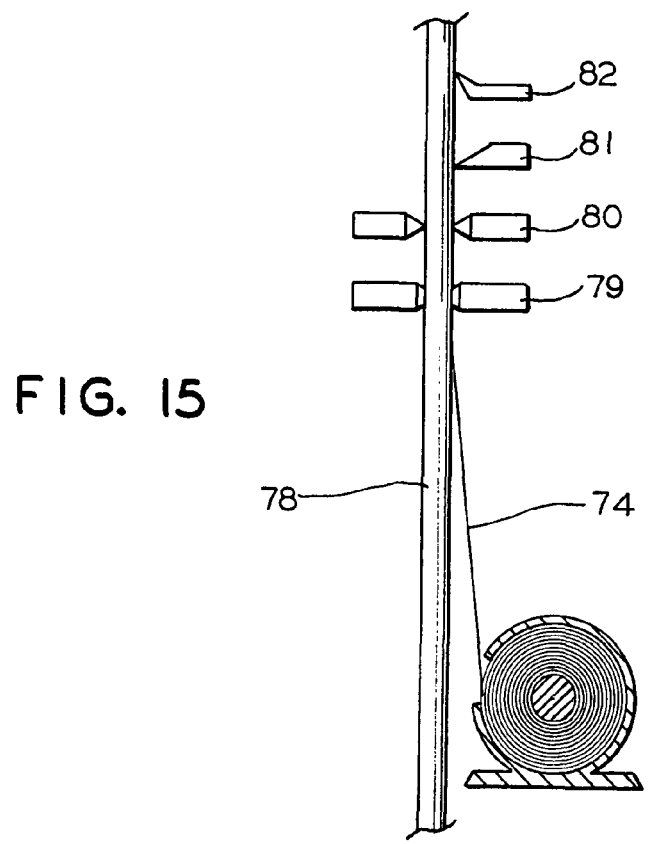
FIG. 15 shows a method of forming a series of sanitary disposable writing instruments of the invention.

As shown in FIG. 15, the at least one sheet 74 of holding material 12 comprises a single sheet and the method includes the step of folding 82 at least an edge portion of the single sheet onto itself and sealing to enclose the holding tube 78.

Figure 16:
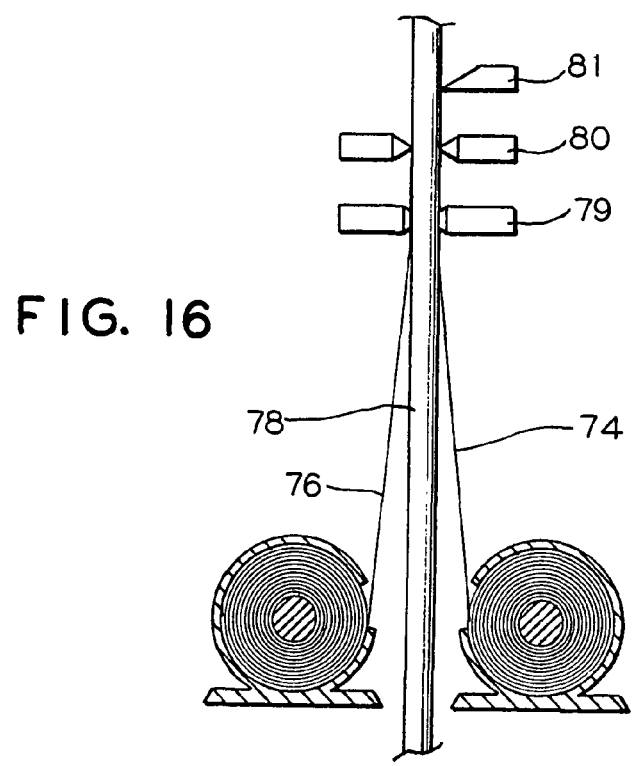
FIG. 16 shows an alternative method of forming a series of sanitary disposable writing instruments of the invention.

According to an alternative method, as shown in FIG. 16, at least two sheets 74, 76 can be fed and the holding tube 78 is fed between these at least two sheets 74, 76 and the sheets are sealed together via sealing means 79 to enclose the holding tube there between. Perforating means 80 and cutting means 81 are also provided.

The writing source or means 28 can include any well known material such as an ink filled tip or a graphite tip 26. The method further includes the step of securing the writing tip 26 in an end portion of the holding tube 78 by any well-known means.

To produce the series 40 of writing instruments illustrated in FIG. 3, an additional step of providing lines of pressure sensitive adhesive 36 onto the at least one sheet 74 of flexible material is required. This embodiment also requires the step of separating the writing instruments from one another and attaching them at alternating opposing ends by means of this pressure sensitive adhesive 36.

As discussed in detail above, the invention provides a novel and inexpensive sanitary disposable writing instrument, a dispenser therefore and a method of producing the writing instrument that minimizes the transfer of bacteria, viruses, chemicals and numerous other contaminants from one person to another.

The invention has been described in such full, clear, concise, and exact terms so as to enable any person skilled in the art to which it pertains to make and use the same. It should be understood that variations, modifications, equivalents and substitutions for components of the specifically described embodiments of the invention may be made by those skilled in the art without departing from the spirit and scope of the invention as set forth in the appended claims. Persons who possess such skill will also recognize that the foregoing description is merely illustrative and not intended to limit any of the ensuing claims to any particular narrow interpretation.

I claim:

1. A sanitary disposable writing instrument for minimizing the transfer of bacteria, viruses and/or chemicals from one person to another, said sanitary disposable writing instrument comprising:
   (a) a strip of flexible holding material having a predetermined size and shape, said strip of holding material having a first portion and a second portion;
   (b) a writing implement having a first end and a second end, said first end of said writing implement extending along and secured to said first portion of said holding material and said second end of said writing implement extending beyond and in a perpendicular direction with respect to an edge of said holding material to form a writing tip;
   (c) a writing means associated with said writing tip;
   (d) a grasping means formed from one of said second portion and said first portion of said holding material to enable the user to grasp one of said first portion and said second portion of said holding material and write with said writing tip; and
   (e) at least a second writing instrument secured thereto with pressure sensitive adhesive to form a series of sanitary disposable writing instruments and wherein upon removal of a first writing instrument from a second writing instrument, said second edge area is rolled into a cylinder and secured with said pressure sensitive adhesive to enclose said writing implement and to form said grasping means.

2. A writing instrument as recited in claim 1 wherein the flexible holding material provides the sole support of the individual writing instruments in the stack.

3. A sanitary disposable writing instrument for minimizing the transfer of bacteria, viruses and/or chemicals from one person to another, said sanitary disposable writing instrument comprising:
   (a) a strip of flexible holding material having a predetermined size and shape, said strip of holding material having a first portion and a second portion, said first portion and said second portion extending in a parallel direction with respect to each other;
   (b) a writing implement having a first end and a second end, said first end of said writing implement extending parallel with said first portion and said second portion when said strip of flexible holding material is in an unfolded condition, said writing implement secured flush against a face surface of said first portion of said holding material and said second end of said writing implement extending beyond and in a perpendicular direction with respect to an edge of said holding material to form a writing tip;
   (c) a writing means associated with said writing tip;
   (d) a grasping means formed from one of said second portion and said first portion of said holding material to enable a user to grasp one of said first portion and said second portion of said holding material and write with said writing tip; and
   (e) at least a second writing instrument secured thereto to form a series of sanitary disposable writing instruments, wherein said series of writing instruments are stacked on top of each other to form a stack of writing instruments and wherein the series of writing instruments are secured together with adhesive along alternating edge portions of the flexible material forming an accordion-shaped stack such that removal of a first writing instrument and its associated flexible holding material causes a second writing instrument and its associated flexible holding material to become positioned for removal from the stack and wherein upon removal of the first writing instrument from the second writing instrument, said second edge area of said first writing instrument is capable of being one of folded or rolled into a cylinder and secured with said adhesive to enclose said writing implement and to form said grasping means and said first edge of said second writing instrument is positioned for subsequent removal from the stack.

4. A writing instrument as recited in claim 3 wherein said first portion of said holding material comprises a first edge area of said strip which is capable of being one of folded and rolled to enclose said writing implement to form said grasping means and said second portion of said holding material is removable from said first portion.

5. A writing instrument as recited in claim 4 wherein said second portion of said holding material is one of a coupon and advertisement which is removable from said first portion of said holding material by means of a frangible area extending between said first and second portion.

6. A writing instrument as recited in claim 3 wherein said writing means comprises one of a pen, pencil, and marker.

7. A writing instrument as recited in claim 3 wherein said series of sanitary disposable writing instruments are secured to one another by means of pressure sensitive adhesive.

8. A writing instrument as recited in claim 3 wherein the flexible holding material provides the sole support of the writing instrument.

9. A writing instrument as recited in claim 7 wherein the series of writing instruments are secured together with a pressure sensitive adhesive extending along alternating first and second edge portions of said flexible holding material.

* * * * *